United States Patent [19]

Ingendoh et al.

[11] Patent Number: 4,847,291
[45] Date of Patent: Jul. 11, 1989

[54] ARYLETHANOL-HYDROXYLAMINES FOR PROMOTION OF LIVESTOCK PRODUCTION

[75] Inventors: Axel Ingendoh, Velbert; Hans Lindel, Leverkusen; Friedrich Berschauer, Wuppertal; Anno de Jong, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 884,709

[22] Filed: Jul. 11, 1986

[30] Foreign Application Priority Data

Jul. 16, 1985 [DE] Fed. Rep. of Germany ....... 3525336

[51] Int. Cl.$^4$ ...................... A61K 31/15; C07C 83/00
[52] U.S. Cl. .................................. 514/524; 514/645; 558/418; 558/422; 564/300
[58] Field of Search ................ 558/422, 418; 564/300; 514/524, 645

[56] References Cited

U.S. PATENT DOCUMENTS 4,407,819 11/1983 Kiernan et al. ..................... 514/524

FOREIGN PATENT DOCUMENTS

| 0026298 | 4/1981 | European Pat. Off. . |
| 1543728 | 2/1970 | Fed. Rep. of Germany . |
| 2351281 | 4/1975 | Fed. Rep. of Germany . |
| 3525336 | 1/1987 | Fed. Rep. of Germany . |
| 2137619 | 10/1984 | United Kingdom . |

OTHER PUBLICATIONS

Chem. Abs., vol. 90, 121317a, "The Synthesis and Oxidation of N-Hydroxy Derivatives of . . . ", Jordan No. 15 (Apr. 1979); p. 518.
Chem. Abs., vol. 98, 88940p, "Derivatives of B-Adrenergic Antagonists . . . ", Zhang et al, No. 11, (Mar. 1983); p. 516.
Australian Journal of Chemistry, "Nitrones and Oxaziridines . . . ", Black et al, vol. 31 (Sep. 1978), pp. 2013-2022.

*Primary Examiner*—Anton H. Sutto
*Attorney, Agent, or Firm*—Sprung Horn Kramer & Woods

[57] ABSTRACT

Aryl ethanol-hydroxylamines of the formula

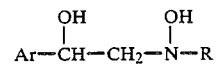

in which
Ar represents aryl or heteroaryl, each of which can optionally be substituted, and
R represents alkyl, aryl, aralkyl, heteroaryl, heteroaralkyl or cycloalkyl, each of which can optionally be substituted, or physiologically tolerated salts thereof, exhibit animal growth-promoting properties. Intermediates therefor of the formula

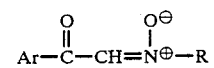

with the exception of phenyl and p-bromophenyl, are also new.

8 Claims, No Drawings

ARYLETHANOL-HYDROXYLAMINES FOR PROMOTION OF LIVESTOCK PRODUCTION

The present invention relates to arylethanol-hydroxylamines, to processes for their preparation and to their use as promoters of production for livestock.

Arylethanolamines are known compounds. Their pharmacological properties differ depending on their chemical structure. Inter alia, certain arylethanolamines have effects on the weight gain of livestock and on the ratio of meat to fat (EP-OS (European Published Specification) No. 26,298). In this context too, the general structure of the arylethanolamine appears to be of crucial importance for the effect.

New arylethanol-hydroxylamines of the formula

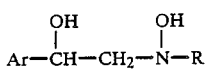

in which
Ar represents aryl or heteroaryl, each of which can optionally be substituted, and
R represents alkyl, aryl, aralkyl, heteroaralkyl, heteroaryl or cycloalkyl, each of which can optionally be substituted,
and their physiologically tolerated salts, enantiomers and diastereomers have been found.

A process for the preparation of the arylethanol-hydroxylamines of the formula I

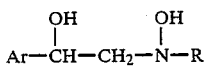

in which
Ar represents aryl or heteroaryl, each of which can optionally be substituted, and
R represents alkyl, aryl, aralkyl, heteroaralkyl, heteroaryl or cycloalkyl, each of which can optionally be substituted,
has been found, which is characterized in that arylglyoxal nitrones of the formula II

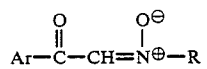

in which
Ar and R have the abovementioned meaning,
are reduced.

The new arylglyoxal nitrones of the formula II

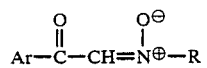

in which
Ar represents aryl or heteroaryl, each of which can optionally be substituted, with the exception of phenyl and p-bromophenyl, and
R represents alkyl, aralkyl, heteroaralkyl or cycloalkyl, each of which can optionally be substituted, have been found.

A process for the preparartion of the new arylglyoxal nitrones of the formula II

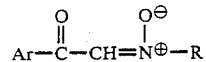

in which
Ar represents aryl or heteroaryl, each of which can optionally be substituted, with the exception of phenyl and p-bromophenyl, and
R represents alkyl, aralkyl, heteroaralkyl or cycloalkyl, each of which can optionally be substituted,
has been found, which is characterized in that arylglyoxals of the formula III

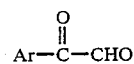

in which
Ar has the abovementioned meaning,
where appropriate in the form of their hydrates or adducts with alcohols, are reacted with hydroxylamines of the formula IV

in which
R has the abovementioned meaning,
with elimination of water.

The arylethanol-hydroxylamines exhibit outstanding production-increasing effects in livestock. Thus they can be used in the area of animal nutrition as promoters of production. This property was astonishing. This is because it was known of arylethanolamines that changes in the substitution of the amine moiety of the molecule give rise to great changes in the biological and pharmacological effect. Thus, it was by no means to be expected that a completely different chemical class of compounds, namely hydroxylamines, exhibit economically utilizable effects. The preferred arylethanol-hydroxylamines of the formula I are those in which Ar represents phenyl, naphthyl, furyl, thienyl, pyrimidinyl, pyrrolyl, thiazolyl, oxazolyl, pyrazolyl, imidazolyl, carbazolyl, fluorenyl, pyridazinyl, carbostyrilyl, indolyl, pyrazinyl, quinolyl, isoquinolyl or pyridyl, each of which can optionally be substituted by one or more identical or different substituents from the group comprising alkyl, halogenoalkyl, aryl, alkoxy, halogenoalkoxy, halogen, nitro, hydroxyl, cyano, alkoxyamino, alkylcarbonyl, amino, aminocarbonyl, dialkylaminocarbonyl, alkyl- and dialkylamino, alkylaminocarbonyl, aminosulphonyl, alkylsulphonyl, alkylsulphinyl, alkylthio, halogenoalkylthio, alkoxycarbonylamino, aminocarbonylamino, alkylenedioxy, halogenoalkylenedioxy, optionally substituted aryl, aryloxy and arylthio, and
R represents straight-chain or branched alkyl, cycloalkyl, bicycloalkyl having up to 12 C atoms, each of which can optionally be substituted by alkynyl, alkenyl, alkoxy, alkylthio, hydroxyl, halogen, optionally substituted aryl, optionally substituted heteroaryl, or aryloxy.

Suitable substituents of the optionally substituted radicals which are preferred are: cyano, halogen such as fluorine, chlorine or bromine, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio and $C_{1-4}$-halogenoalkylthio. In the case where the substituents are located on a phenyl radical, additionally preferred methylenedioxy, ethylenedioxy, halogen-substituted methylenedioxy and halogen-substituted ethylenedioxy, furthermore phenyl or phenoxy which in turn can carry one or more of the abovementioned substituents.

The compounds of the formula I which are particularly preferred are those in which Ar represents phenyl which is substituted one or several times by identical or different radicals from the group comprising $C_{1-4}$-alkyl, phenyl, $C_{1-4}$-alkoxy, halogen, cyano, nitro, $C_{1-4}$-halogenoalkyl, amino $C_{1-4}$-alkylamino, di-($C_{1-4}$)-alkylamino, $C_{1-4}$-alkoxycarbonyl, aminocarbonyl, $C_{1-4}$-alkylaminocarbonyl, di-($C_{1-4}$)-alkylaminocarbonyl, aminosulphonyl, $C_{1-4}$-alkylaminosulphonyl, di-($C_{1-4}$)-alkylaminosulphonyl, $C_{1-4}$-alkylsulphonyl, $C_{1-4}$-alkylsulphinyl, $C_{1-4}$-alkylthio, $C_{1-4}$-alkoxycarbonylamino and hydroxyl, $C_{1-4}$-halogenoalkoxy, $C_{1-4}$-halogenoalkylthio, methylenedioxy, ethylenedioxy, halogenomethylenedioxy, and phenoxy which in turn can be substituted by one of the radicals mentioned, R represents stright-chain or branched alkyl, cycloalkyl or bicycloalkyl having up to 12 C atoms, each of which is optionally substituted by $C_{2-4}$-alkynyl, $C_{2-4}$-alkenyl, hydroxyl, halogen and phenyl which is optionally substituted by halogen, $C_{1-4}$-alkoxy, $C_{1-4}$-alkyl and nitro.

Furthermore, compounds of the formula I in which

Ar represents phenyl which is substituted by one, two or three identical or different radicals from the group comprising phenyl, $C_{1-4}$-alkyl, $C_{1-4}$-halogenoalkyl, cyano, hydroxyl, amino, $C_{1-4}$-alkyl and di-$C_{1-4}$-alkylamino, halogen and nitro, and R represents straight-chain or branched alkyl, or cycloalkyl which has up to 8 C atoms and is optionally substituted by $C_{2-4}$-alkynyl, $C_{2-4}$-alkenyl, hydroxyl, halogen, and phenyl which is optionally substituted by methoxy, $C_{1-4}$-alkyl, nitro, $CF_3$, and halogen.

Particular mention may be made of compounds of the formula I in which

Ar represents phenyl which is substituted by fluorine, chlorine, bromine, amino and CN, and R represents $C_{1-5}$-alkyl which is optionally susbstituted by $C_{3-6}$-cycloalkyl, ethynyl, hydroxyl, halogen, or phenyl which in turn is optionally substituted by halogen, trifluoromethyl or methoxy.

In addition to the compounds mentioned in the examples, the following compounds of the formula I may be mentioned specifically:

| Ar | R |
|---|---|
| 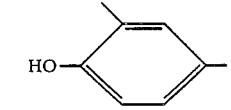 | $CH_3$ |
| 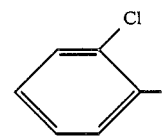 | $C(CH_3)_3$ |
| 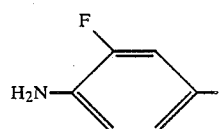 | $C(CH_3)_3$ |
| 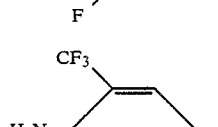 | $C(CH_3)_3$ |
| 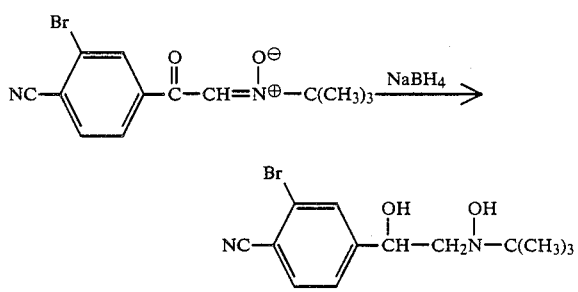 | $C(CH_3)_3$ |

The compounds of the formula I can also exist in the form of their enantiomers or, if several optically active C atoms are present in the molecule, in the form of their diastereomers.

Physiologically tolerated salts of the compounds of the formula I can be formed with the following acids:

Hydrochloric acid, sulphuric acid, phosphoric acid, perchloric acid, hydrobromic, hydroiodic and hydrofluoric acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acid, formic acid, chloroacetic acid, toluenesulphonic acid, benzenesulphonic acid, trichloroacetic acid, phthalic acid, naphthalenesulphonic acid and nicotinic acid.

The compounds of the formula I are obtained by reduction of arylglyoxal nitrones of the formula II. One reduction is illustrated by the following equation:

Some arylglyoxal nitrones of the formula II are new (compare D. Black. et. al. Aust. j. Chem. (1978) 31 2013-22). Their preparation is described below. The arylglyoxal nitrones of the formula II which are preferably used are those in which the radicals Ar and R have the meanings indicated as preferred for the compounds of the formula I.

The reaction is preferably carried out with the following reducing agents: complex hydrides such as, for example, alkali metal borohydrides such as, for example, NaBH$_4$, NaBH$_3$CN, LiBH$_4$ and NaBH$_x$(O-alkyl)$_y$, the sum of x and y being 4. NaBH$_4$ is particularly preferred.

The reaction is preferably carried out in inert organic solvents as diluents. These include, in particular, aliphatic and aromatic, optionally halogenated, hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, as well as ethers such as diethyl and dibutyl ethers, glycol dimethyl ether and diglycol dimethyl ether, tetrahydrofuran and dioxane, also alcohols such as methanol, ethanol, isopropanol or longer-chain alcohols, in addition esters such as methyl and ethyl acetate, also nitriles such as, for example, acetonitrile and propionitrile, benzonitrile and glutarodinitrile, furthermore amides such as, for example, dimethylformamide, dimethylacetamide and N-methylpyrrolidone, as well as dimethyl sulphoxide, tetramethylene sulphone and hexamethylphosphoric triamide.

The reaction is carried out at temperatures of −50° to 100° C., preferably at temperatures between 0° C. and 50° C.

Working up is carried out in a customary manner.

Arylglyoxal nitrones of the formula II are new. They are obtained by reaction of arylglyoxals of the formula III with N-alkylhydroxylamines of the formula IV. The reaction can be represented by the following equation:

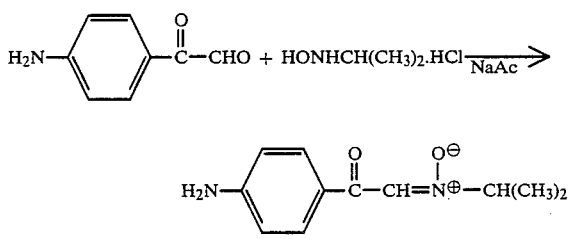

Some arylglyoxals of the formula III are known. New arylglyoxals can be prepared by processes known per se, for example by oxidation of the corresponding α-halogenoacetophenones with DMSO, or oxidation of acetophenones with selenium dioxide.

The arylglyoxals of the formula III which are preferably used are those in which Ar has the meanings indicated as preferred for the compounds of the formula I.

The following arylglyoxals may be mentioned specifically:

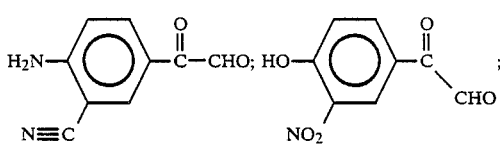

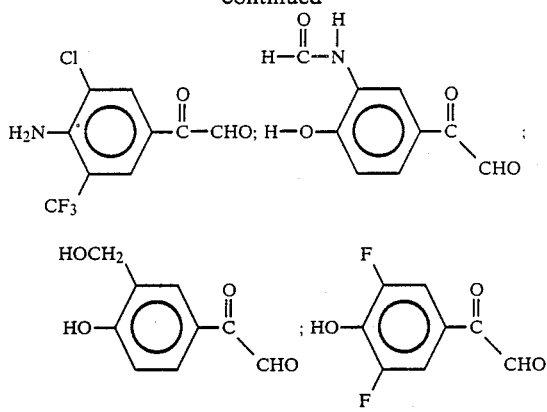

Hydroxylamines of the formula IV are known or can be prepared by methods known per se. The hydroxylamines of the formula IV which are preferably used are those in which R has the meanings indicated as preferred for the compounds of the compound I.

The reaction can be carried out with or without diluents. All inert organic solvents may be used as diluents. These include in particular, aliphatic and aromatic, optionally halogenated, hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, alcohols such as methanol, ethanol, isopropanol, glycol and longer-chain alcohols, furthermore ethers such as diethyl and diethyl ethers, glycol dimethyl ether and diglycol dimethyl ether, tetrahydrofuran and dioxane, in addition ketones such as acetone, methyl ethyl, methyl isopropyl and methyl isobutyl ketones, moreover esters such as methyl and ethyl acetate, furthermore nitriles such as, for example, acetonitrile and propionitrile, benzonitrile and glutarodinitrile, in addition amides such as, for example, dimethylformamide, dimethylacetamide and N-methylpyrrolidone, as well as dimethyl sulphoxide, tetramethylene sulphone and hexamethylphosphoric triamide.

It is preferable to react the N-alkylhydroxylamine of the general formula IV as a salt of an inorganic or organic acid with the arylglyoxal of the general formula III in the presence of an alkali metal salt of a weak organic acid such as, for example, sodium acetate.

The reaction can be carried out at temperatures of 10°–200° C., preferably of 50°–150° C., very particularly preferably at the boiling point of the solvent.

It is preferably carried out in the presence of a water-removing agent. Examples of these which may be mentioned are Na$_2$SO$_4$, MgSO$_4$, K$_2$CO$_3$, CaCl$_2$, molecular sieves, silica gel and aluminum hydroxides. The water produced in the reaction can also be removed from the reaction mixture azeotropically.

The compounds of the formula I are preferably used in equimolar ratio.

The working up is carried out in a manner known per se.

It is not necessary in every case to isolate the arylglyoxal nitrone of the general formula II for the preparation of arylethanol-hydroxylamines of the general formula I. It may prove to be particularly favorable to carry out the reaction sequence in a one-pot reaction.

The active compounds are used as production promoters of livestock for the promotion and acceleration of growth, of the production of milk and wool, and for the improvement of the feed efficiency, the quality of meat and for displacement of the meat/fat ratio in favor of meat. The active compounds are used for useful, breeding, ornamental and hobby livestock.

The useful and breeding livestock include mammals such as, for example, cattle, pigs, horses, sheep, goats, rabbits, hares, fallow deer, fur-bearing animals such as mink and chinchilla, poultry such as, for example, chickens, geese, ducks, turkeys and pigeons, fish, such as, for example, carp, trout, salmon, eels, tench and pike, and reptiles such as, for example, snakes and crocodiles.

The ornamental and hobby livestock includes mammals such as dogs and cats, birds such as parrots and canaries, and fish such as ornamental and aquarium fish, for example goldfish.

The active compounds are used irrespective of the sex of the livestock during all phases of growth and production of the livestock. The active compounds are preferably used during the phase of intensive growth and production. Depending on the species, the phase of intensive growth and production lasts from one month up to 10 years.

The amount of the active compounds which is administered to the livestock to achieve the desired effect can be varied within wide limits because of the favorable properties of the active compounds. It is preferably about 0.001 to 50 mg/kg, in particular 0.01 to 5 mg/kg, of body weight per day. The appropriate amount of the active compound and the appropriate duration of the administration depend, in particular, on the species, the age, the sex, the phase of growth and production, the state of health and the nature of the housing and feeding of the livestock, and can readily be determined by all those skilled in the art.

The active compounds are administered to the livestock by customary methods. The mode of administration depends, in particular, on the species, the behaviour and the state of health of the livestock.

The active compounds can be utilized once. However, it is also possible for the active compounds to be administered temporarily or continuously throughout the entire, or throughout a part, of the phase of growth and production.

With continuous administration, the administration can take place once or several times a day, at regular or irregular intervals.

The administration is carried out orally or parenterally, in formulations suitable for this purpose or in the pure form.

The active compounds can be present in the formulations alone or mixed with other production-promoting active compounds, mineral feedstuffs, trace element compounds, vitamins, non-protein compounds, colorants, antioxidants, flavourings, emulsifiers, flow regulators, preservatives and pelleting auxiliaries.

Other production-promoting active compounds are: for example antibiotics such as tylosin and virginiamycin. Examples of mineral feedstuffs are dicalcium phosphate, magnesium oxide and sodium chloride. Examples of trace element compounds are iron fumarate, sodium iodide, cobalt chloride, copper sulphate and zinc oxide. Examples of vitamins are vitamin A, vitamin $D_3$, vitamin E, B vitamins and vitamin C. Examples of non-protein compounds are biuret and urea. Examples of colorants are carotenoids such as citranaxanthine, zeaxanthine and capsanthine. Examples of antioxidants are ethoxyquin and butylhydroxy-toluene. Examples of flavourings are vanillin. Examples of emulsifiers are esters of lactic acid, and lecithin. Examples of flow regulators are sodium stearate and calcium stearate. Examples of preservatives are citric acid and propionic acid. Examples of pelleting auxiliaries are ligninsulphonates and cellulose ethers.

The active compounds can also be administered together with the feed and/or the drinking water.

The feed includes non-compound feedstuffs of vegetable origin, such as hay, roots and cereals byproducts, non-compound feedstuffs of animal origin, such as meat, fats, milk products, bonemeal and fish products, the non-compound feedstuffs such as vitamins, proteins, amino aicds, for example DL-methionine, and salts such as lime and sodium chloride. The feed also includes supplementary, compound and mixed feedstuffs. These contain non-compound feedstuffs in a composition which ensure a balanced diet with regard to the supply of energy and protein and the supply of vitamins, mineral salts and trace elements.

The concentration of the active compounds in the feed is normally about 0.01–500 ppm, preferably 0.1–50 ppm.

The active compounds can be added as such, or in the form of premixes or feed concentrates, to the feed.

Example for the composition of a chicken rearing feed which contains an active compound according to the invention:

200 g of wheat, 340 g of corn, 361 g of soy meal, 60 g of beef tallow, 15 g of dicalcium phosphate, 10 g of calcium carbonate, 4 g of iodized sodium chloride, 7.5 g of vitamin/mineral mix and 2.5 g of active compound premix provide, after careful mixing, 1 kg of feed. 1 kg of feed mix contains the following: 600 I.U. of vitamin A, 100 I.U. of vitamin, $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSo_2 \times H_2O$, 140 mg of $ZnSo_4 \times 7H_2O$, 100 mg of $FeSo_4 \times 7H_2O$ and 20 mg of $CuSo_4 \times 5H_2O$.

2.5 g of active compound premix contain, for example, 10 mg of active compound, 1 g of DL-methion, and the remainder soy bean meal.

Example for the composition of a pig rearing feed which contains an active compound according to the invention:

630 g of feed cereal meal (composed of 200 g of corn, 150 g of barley meal, 150 g of oatmeal and 130 g of wheatmeal), 80 g of fishmeal, 60 g of soy meal, 60 g of cassava meal, 38 g of brewers' yeast, 50 g of vitamin/mineral mix for pigs, 30 g of linseed cake meal, 30 g of corn gluten feed, 10 g of soy oil, 10 g of sugar cane molasses and 2 g of compound premix (composition, for example, as for chicken feed) provide, after careful mixing, 1 kg of feed.

The feed mixes indicated are designated for the rearing and fattening of, preferably, chickens and pigs, but they can also be used, in the same or similar composition, for the feeding of other livestock.

EXAMPLE A

Rat feeding trial

Female laboratory rats weighing 90–110 g of the type SPF Wistar (bred by Hagemann) are fed ad lib. with standard rat feed to which the desired amount of active compound has been added. Each trial arrangement is carried out with feed of the identical batch so that differences in the composition of the feed cannot impair the comparability of the results.

The rats receive water ad lib.

12 rats form each trial group and they are fed with feed to which the desired amount of active compound has been added. A control group receives feed containing no active compound. The mean body weight and the variation in the body weights of the rats are the same in each trial group so that comparability of the trial groups with one another is ensured.

The weight gain and feed consumption during the 13-day trial are determined.

The results obtained are shown in the table:

TABLE 1

| Rat feeding trial | | |
|---|---|---|
| Active compound example no. | Active compound added ppm. | Body weight gain in 13 days in g |
| Control | 0 | 36.4 |
| 5 | 1 | 40.0 |
|  | 25 | 47.3 |
| 4 | 25 | 45.5 |
| 14 | 25 | 45.1 |
| 27 | 25 | 43.0 |

EXAMPLES

EXAMPLE 1

N-t-butyl-N-2-hydroxy-2-phenyl-ethyl-hydroxylamine

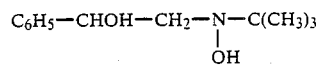

1.8 g of NaBH$_4$ were added in portions, at room temperature, to 5 g of N-t-butyl-phenylglyoxal nitrone dissolved in 150 ml of methanol. After 3 to 4 hours, the mixture was evaporated in a rotary evaporator, 100 ml of 10% strength HCl were added to the residue in the cold, the mixture was extracted three times with 25 ml of ether, and the aqueous phase was made alkaline with 120 ml of 10% strength aqueous sodium hydroxide solution, while cooling. The aqueous phase was extracted several times with dichloromethane, and the organic phase was dried over sodium suphate and evaporated. The residue was dissolved in 50 ml of ether, and 150 ml of a saturated ethereal solution of oxalic acid were added. The precipitate of the oxalate which thus resulted was isolated and recrystallized.

Yield: 2.7 g.

Melting point: 143°–144° C.

The following compounds of the formula I were obtained analogously.

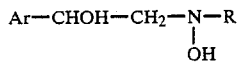

| Example | Ar | R | Melting point °C. |
|---|---|---|---|
| 2 | C$_6$H$_5$ | —CH(CH$_3$)$_2$ | 123° C. (oxalate) |
| 3 | C$_6$H$_5$ | CH$_3$ | 104° C. (oxalate) |
| 4 | 4-NH$_2$,3,5-Cl$_2$—C$_6$H$_2$ | —CH(CH$_3$)$_2$ | 148° C. (oxalate) |
| 5 | 4-NH$_2$,3,5-Cl$_2$—C$_6$H$_2$ | —C(CH$_3$)$_3$ | 95–100° C. (oxalate) |
| 6 | 4-NH$_2$,3,5-Cl$_2$—C$_6$H$_2$ | —C(CH$_3$)$_2$C≡CH | 76–85° C. (oxalate) decomp. |
| 7 | 4-NH$_2$,3,5-Cl$_2$—C$_6$H$_2$ | —CH(CH$_3$)—CH$_2$—2-CH$_3$O—C$_6$H$_4$ | oil |
| 8 | 4-NH$_2$,3,5-Cl$_2$—C$_6$H$_2$ | —C(CH$_3$)—C$_2$H$_5$ | 72–75° C. (oxalate) |
| 9 | 4-NH$_2$,3,5-Cl$_2$—C$_6$H$_2$ | —CH(CH$_3$)—CH$_2$—2-F—C$_6$H$_4$ | 90° C. (oxalate) decomp. |
| 10 | 4-NH$_2$,3,5-Cl$_2$—C$_6$H$_2$ | —CH(CH$_3$)—CH$_2$—4-CH$_3$O—C$_6$H$_4$ | 78° C. (oxalate) |
| 11 | 4-NH$_2$,3,5-Cl$_2$—C$_6$H$_2$ | —CH(CH$_3$)—CH$_2$—3-CF$_3$—C$_6$H$_4$ | oil |
| 12 | 4-NH$_2$,3,5-Cl$_2$—C$_6$H$_2$ | —CH(CH$_3$)—CH$_2$—3,4-CH$_3$O—C$_6$H$_3$ | 115° C. |
| 13 | 4-NH$_2$,3,5-Cl$_2$—C$_6$H$_2$ | —CH$_2$—CH(CH$_3$)$_2$ | oil |
| 14 | 4-NH$_2$,3,5-Cl$_2$—C$_6$H$_2$ | —C(CH$_3$)$_2$—CH$_2$OH | 85° C. (oxalate) |
| 15 | 4-NH$_2$,3,5-Cl$_2$—C$_6$H$_2$ | —CH(CH$_3$)—CH$_2$—2-F,6-Cl—C$_6$H$_3$ | 76° C. (oxalate) |
| 16 | 4-NH$_2$,3,5-Cl$_2$—C$_6$H$_2$ | —CH$_2$—C(CH$_3$)$_3$ | 108° C. (oxalate) |
| 17 | 4-NH$_2$,3,5-Cl$_2$—C$_6$H$_2$ | —CH(CH$_3$)—CH$_2$—4-F—C$_6$H$_4$ | oil |
| 18 | 4-NH$_2$,3,5-Cl$_2$—C$_6$H$_2$ | —CH$_2$—CH$_2$—(3,4-(OCH$_3$)$_2$—C$_6$H$_3$) | oil |
| 19 | 4-NH$_2$,3,5-Cl$_2$—C$_6$H$_2$ | —CH(cyclo-C$_3$H$_5$)$_2$ | oil |
| 20 | 4-NH$_2$,3,5-Cl$_2$—C$_6$H$_2$ | —CH(CH$_3$)—CH$_2$—3-Cl—C$_6$H$_4$ | solid (oxalate) |
| 21 | 4-NH$_2$,3,5-Cl$_2$—C$_6$H$_2$ | —CH(CH$_3$)—CH$_2$—2,6-Cl$_2$—C$_6$H$_3$ | solid (oxalate) |
| 22 | 4-NH$_2$,3,5-Cl$_2$—C$_6$H$_2$ | piperidino | solid (oxalate) |
| 23 | 4-NH$_2$,3,5-Cl$_2$—C$_6$H$_2$ | cyclohexyl | oxalate |

-continued $$Ar-CHOH-CH_2-N(OH)-R$$

| Example | Ar | R | Melting point °C. |
|---|---|---|---|
| 24 | 4-NH$_2$,3,5-Cl$_2$—C$_6$H$_2$ | (cyclopentyl) | oxalate |
| 25 | 4-NH$_2$,3,5-Cl$_2$—C$_6$H$_2$ | —nC$_4$H$_9$ | oxalate |
| 26 | 4-NH$_2$,3,5-Cl$_2$—C$_6$H$_2$ | —CH(CH$_3$)C(CH$_3$)$_3$ | oxalate |
| 27 | 4-NH$_2$—,3-Cyano-C$_6$H$_3$ | —CH(CH$_3$)$_2$ | 51° C. |
| 28 | 4-NH$_2$—,3-Cyano-C$_6$H$_3$ | —C(CH$_3$)$_3$ | 59° C. |
| 29 | 4-NH$_2$—,3-Cyano-C$_6$H$_3$ | —C(CH$_3$)$_2$—CH$_2$OH | oil |
| 30 | 4-OH—C$_6$H$_4$— | C(CH$_3$)$_3$ | Oil |
| 31 | 4-NO$_2$—C$_6$H$_4$— | C(CH$_3$)$_3$ | Oil |
| 32 | 2-Naphthyl | C(CH$_3$)$_3$ | Oil |
| 33 | 4-NH$_2$,3,5-CH$_2$—C$_6$H$_2$— | CH$_3$ | 67° C. |
| 34 | 4-Phenyl—C$_6$H$_4$— | C(CH$_3$)$_3$ | 69° C. |
| 35 | 4-OH,3-NO$_2$—C$_6$H$_3$— | C(CH$_3$)$_3$ | 69 (oxalate) |
| 36 | 4-NH$_2$,3-Cl,5—CF$_3$—C$_6$H$_2$— | C(CH$_3$)$_3$ | Oil |
| 37 | 4-NH$_2$,3,5-Cl$_2$—C$_6$H$_2$— | CH(CH$_3$)CF$_3$ | 136 (oxalate) |
| 38 | 4-NH$_2$,3-5-Cl$_2$—C$_6$H$_2$— | CH$_2$—CF$_3$ | Oil |
| 39 | 4-NH$_2$,3-5-Cl$_2$—C$_6$H$_2$— | (2-methylcyclohexyl) | Oil |
| 40 | 4-NH$_2$,3-5-Cl$_2$—C$_6$H$_2$— | —CH(CH$_3$)—CH$_2$—OH | Oil |
| 41 | 4-NH$_2$,3-5-Cl$_2$—C$_6$H$_2$— | —CH(CH$_3$)—C$_3$H$_7$ | Oil |
| 42 | 4-NH$_2$,3-5-Cl$_2$—C$_6$H$_2$— | —CH(C$_2$H$_5$)$_2$ | Oil |
| 43 | 4-NH$_2$,3-5-Cl$_2$—C$_6$H$_2$— | —CH(CH$_3$)CH(CH$_3$)$_2$ | Oil |
| 44 | 3,4-Cl$_2$—C$_6$H$_3$— | —C(CH$_3$)$_3$ | Oil |
| 45 | 4-NH$_2$,3,5-Cl$_2$—C$_6$H$_2$— | —CH(CH$_3$)—CH$_2$—O—(3-NO$_2$-4-CH$_3$-C$_6$H$_3$) | 59–62 |
| 46 | 4-OH,3-CH$_3$OCO—C$_6$H$_3$— | —C(CH$_3$)$_3$ | 138–140 |
| 47 | 3,5-Cl$_2$,4-CH$_3$O—C$_6$H$_2$— | —C(CH$_3$)$_3$ | 175–177 |
| 48 | 5-Cl,4-NO$_2$—C$_6$H$_3$— | —C(CH$_3$)$_3$ | 94 |
| 49 | 3,5-Cl$_2$,4-NH$_2$—C$_6$H$_2$— | —C(CH$_3$)$_3$ | 173–174 (fumarate) |
| 50 | 4-CH$_3$CO,3-CH$_3$S—C$_6$H$_3$— | —C(CH$_3$)$_3$ | (F$_f$ value on DC silica F254, 0.2 mm, flowing agent Toluene, Ethanol = 3:1 = 0.365) |
| 51 | 4-OH,3-HOCH$_2$—C$_6$H$_3$— | —C(CH$_3$)$_3$ | Oil |
| 52 | 4-OH,3-CH$_3$SO$_2$NH—C$_6$H$_3$— | i-Propyl | 135 |
| 53 | 2,5-CH$_3$—C$_6$H$_3$ | —C(CH$_3$)$_3$ | Oil |

PREPARATION OF THE STARTING MATERIAL

EXAMPLE A1

N-1,3,3-trimethyl-propyl-phenylglyoxal adonitrone

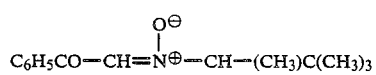

5 g of 3,3-dimethyl-2-butyl-hydroxylamine HCl, 2.6 g of sodium acetate and 5.7 g of phenylglyoxal hydrate were stirred in 100 ml of ethanol at room temperature for 2.5 hours. The mixture was filtered, the filtrate was evaporated to 10 ml, and 20 ml of water were added to it. After cooling at 1° C. for one hour, the resulting precipitate was filtered off and recrystallized from methanol/water.

Yield: 5 g.

Melting point: 134°–135° C.

The following compounds of the formula II were obtained analogously:

| Example | Ar | R | Melting point: |
|---|---|---|---|
| a2 | C$_6$H$_5$ | —CH(CH$_3$)$_2$ | 92–93° C. |
| a3 | C$_6$H$_5$ | —CH$_3$ | 90–94° C. |

-continued

| Example | Ar | R | Melting point: |
|---|---|---|---|
| a4 | C$_6$H$_5$ | —C(CH$_3$)$_3$ | 79° C. |
| a5 | 4-NH$_2$,3,5-Cl$_2$—C$_6$H$_2$ | —CH$_3$ | 122° C. |
| a6 | 4-NH$_2$,3,5-Cl$_2$—C$_6$H$_2$ | —C(CH$_3$)$_3$ | 173° C. decomp. |
| a7 | 4-NH$_2$,3,5-Cl$_2$—C$_6$H$_2$ | —CH(CH$_3$)$_2$ | 155° C. decomp. |
| a8 | 4-NH$_2$,3,5-Cl$_2$—C$_6$H$_2$ | —C(CH$_3$)$_2$C≡CH | 113–120° C. decomp. |
| a9 | 4-NH$_2$,3,5-Cl$_2$—C$_6$H$_2$ | —C(CH$_3$)$_2$C$_2$H$_5$ | 118–120° C. |
| a10 | 4-NH$_2$,3,5-Cl$_2$—C$_6$H$_2$ | —CH(CH$_3$)—CH$_2$—2-F—C$_6$H$_4$ | oil |
| a11 | 4-NH$_2$,3,5-Cl$_2$—C$_6$H$_2$ | —CH(CH$_3$)—CH$_2$—3-CF$_3$—C$_6$H$_4$ | oil |
| a12 | 4-NH$_2$,3,5-Cl$_2$—C$_6$H$_2$ | —CH(CH$_3$)—CH$_2$—2-CH$_3$O—C$_6$H$_4$ | oil |
| a13 | 4-NH$_2$,3,5-Cl$_2$—C$_6$H$_2$ | —CH(CH$_3$)—CH$_2$—3,4-CH$_3$O—C$_6$H$_3$ | oil |
| a14 | 4-NH$_2$,3,5-Cl$_2$—C$_6$H$_2$ | —CH(CH$_3$)—CH$_2$—4-CH$_3$O—C$_6$H$_4$ | oil |
| a15 | 4-NH$_2$,3,5-Cl$_2$—C$_6$H$_2$ | —C(CH$_3$)$_2$—CH$_2$OH | oil |
| a16 | 4-NH$_2$,3,5-Cl$_2$—C$_6$H$_2$ | —CH(cyclo-C$_3$H$_5$)$_2$ | oil |
| a17 | 4-NH$_2$,3,5-Cl$_2$—C$_6$H$_2$ | —CH(CH$_3$)(CF$_3$) | oil |
| a18 | 4-NH$_2$,3,5-Cl$_2$—C$_6$H$_2$ | —CH$_2$CF$_3$ | oil |
| a19 | 4-NH$_2$,3,5-Cl$_2$—C$_6$H$_2$ | —CH$_2$—C(CH$_3$)$_3$ | oil |
| a20 | 4-NH$_2$,3,5-Cl$_2$—C$_6$H$_2$ | —CH$_2$—CH(CH$_3$)$_2$ | oil |
| a21 | 4-NH$_2$,3,5-Cl$_2$—C$_6$H$_2$ | —CH(CH$_3$)CH$_2$—4-F—C$_6$H$_4$ | oil |
| a22 | 4-NH$_2$,3,5-Cl$_2$—C$_6$H$_2$ | —CH(CH$_3$)—CH$_2$—2-Cl,6—F—C$_6$H$_3$ | oil |
| a23 | 4-NH$_2$,3,5-Cl$_2$—C$_6$H$_2$ | —CH$_2$—CH$_2$—3,4-CH$_3$O—C$_6$H$_4$ | oil |

EXAMPLE B

The new hydroxylamines in the following table were prepared by known processes.

Process (a)=W. D. Emmons, J. Amer. Chem. Soc. 79, 5739–54, (1957)

Process (b)=R. Borch, J. Am. Chem. Soc. 93, 2897, (1971).

| Example No. | Formula | Process |
|---|---|---|
| b14 | 2-CF₃-C₆H₄-CH₂CH₂-NHOH | (b) |
| b15 | 2-methylcyclohexyl-NHOH | (b) |
| b16 | (C₂H₅)₂—CH—NHOH | (b) |
| b17 | (CH₃)₂CH—CHCCH₃—NHOH | (b) |
| b18 | CH₃(CH₂OH)—CHNHOH | (b) |
| b19 | (nC₃H₇)CH₃—CHNHOH | (b) |
| b20 | ((CH₃)₂CH)CH₃—CHNHOH | (b) |
| b21 | (C₂H₅)₂—CHNHOH | (b) |

It will be understood that the specification and examples are illustrative but not limitative of the present invention and that other embodiments within the spirit and scope of the invention will suggest themselves to those skilled in the art.

We claim:

1. An arylethanol-hydroxylamine of the formula

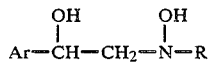

in which

Ar is phenyl substituted in 3-position by Cl, CH₃, CN or CH₃SO₂NH, in 4-position by NH₂ or OH and in 5-position by Cl or CF₃, and R is alkyl of 3 to 5 carbon atoms, which may be substituted once with OH, cyclohexyl, cyclohexyl substituted once with a CH₃ group, and ethyl substituted in the 2 carbon atom with a methoxyphenyl group, or a physiologically tolerated salt thereof.

2. A method of promoting growth of animals which comprises supplying to said animals a growth promoting effective amount of a compound or salt according to claim 1.

3. A compound according to claim 1, wherein such compound is N-2-(4-amino-3,5-dichloro-phenyl)-2-hydroxy-ethyl-N-isopropyl-hydroxylamine of the formula

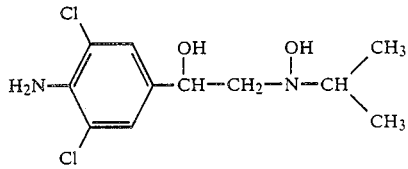

or a physiologically tolerated salt thereof.

4. A compound according to claim 1, wherein such compound is N-2-(4-amino-3,5-dichloro-phenyl)-2-hydroxy-ethyl-N-t-butyl-hydroxylamine of the formula

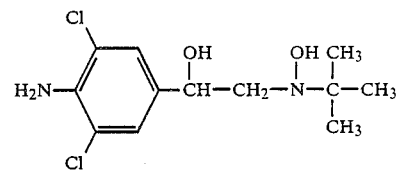

or a physiologically tolerated salt thereof.

5. A compound according to claim 1, wherein such compound is N-2-(4-amino-3,5-dichloro-phenyl)-2-hydroxy-ethyl-N-hydroxy-t-butyl-hydroxylamine of the formula

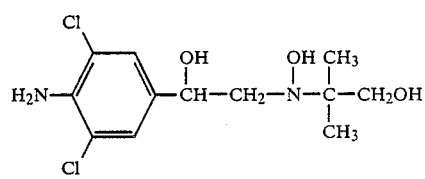

or a physiologically tolerated salt thereof.

6. A compound according to claim 1, wherein such compound is N-2-(4-amino-3-cyano-phenyl)-2-hydroxy-ethyl-N-isopropyl-hydroxylamine of the formula

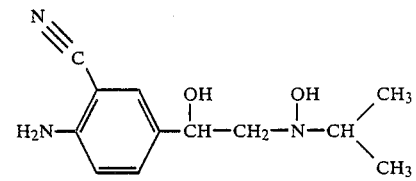

or a physiologically tolerated salt thereof.

7. An animal growth promoting composition comprising a growth promoting effective amount of a compound or salt according to claim 1 and a diluent.

8. The method according to claim 2, wherein such compound is
N-2-(4-amino-3,5-dichloro-phenyl)-2-hydroxy-ethyl-N-isopropyl-hydroxylamine,
N-2-(4-amino-3,5-dichloro-phenyl)-2-hydroxy-ethyl-N-t-butyl-hydroxylamine,
N-2-(4-amino-3,5-dichloro-phenyl)-2-hydroxy-ethyl-N-hydroxy-t-butyl-hydroxylamine or
N-2-(4-amino-3-cyano-phenyl)-2-hydroxy-ethyl-N-isopropyl-hydroxylamine
or a physiologically tolerated salt thereof.

* * * * *